United States Patent [19]

Randall

[11] 3,947,594
[45] Mar. 30, 1976

[54] 4-HALO-1-HYDROXYANTHRAQUINONE CONTAINING FUNGICIDAL COMPOSITION
[75] Inventor: David I. Randall, Easton, Pa.
[73] Assignee: GAF Corporation, New York, N.Y.
[22] Filed: Dec. 18, 1974
[21] Appl. No.: 534,147

Related U.S. Application Data
[63] Continuation of Ser. No. 358,081, May 7, 1973, abandoned.

[52] U.S. Cl. ............... 424/331; 424/289; 424/294; 424/295; 424/303; 424/311; 424/DIG. 8
[51] Int. Cl.² ... A01N 9/00; A01N 9/14; A01N 9/24
[58] Field of Search ...... 424/DIG. 8, 289, 294, 295, 424/303, 311, 331

[56] References Cited
UNITED STATES PATENTS
2,396,019  3/1946  Murray ........................ 424/294 X
3,558,787  1/1971  Harmon ........................ 424/331
3,705,914  12/1972  Pickles et al. ................ 260/396 R Primary Examiner—Jerome D. Goldberg
Assistant Examiner—Allen J. Robinson
Attorney, Agent, or Firm—Walter C. Kehm

[57] ABSTRACT

Fungicidally active compounds, compositions containing the same and methods for making and using such compounds wherein the fungicidally active compounds include 1-substituted anthraquinones (and the acyl esters, carbamates and carbonates thereof), the 1-substituted anthraquinone having the formula:

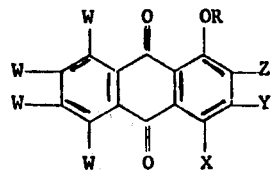

wherein R is hydrogen or acyl, X is halo such as chloro, fluoro or bromo, Z is hydrogen, halo such as chloro, fluoro or bromo, nitro, sulfo or lower alkyl, Y is hydrogen, halo or lower alkyl, and W is hydrogen, hydroxy, halo or lower alkyl. Preferably R is hydrogen, X is halo, Z is hydrogen, halo such as chloro, fluoro or bromo or lower alkyl, Y is hydrogen, chloro or lower alkyl, and W is hydrogen, alkyl or chloro.

7 Claims, No Drawings

4-HALO-1-HYDROXYANTHRAQUINONE CONTAINING FUNGICIDAL COMPOSITION

This is a continuation of application Ser. No. 358,081, filed May 7, 1973, now abandoned.

The 1-substituted anthraquinones as set out hereinafter are novel:

a. compounds of the formula:

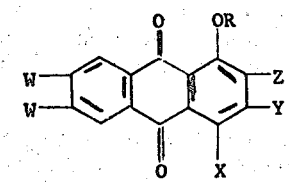

II wherein R is hydrogen or acyl, Y is a member selected from the group consisting of chloro, bromo, fluoro, lower alkyl and hydrogen, Z is a member from the group consisting of chloro, bromo, fluoro, nitro, lower alkyl and hydrogen, W is a member selected from the group consisting of chloro and hydrogen with the proviso that when W is chloro, X is a member selected from the group consisting of chloro, bromo and fluoro, and when W is hydrogen, X is fluoro, b. the carbonates, carbamates and metal salts of said group member (a) wherein R is hydrogen, and c. the carbonates and carbamates of the compounds of the formula:

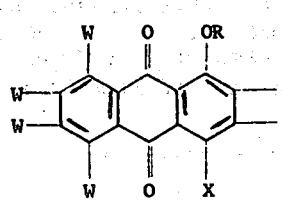

I wherein R is hydrogen, W is a member selected from the group consisting of hydrogen, hydroxy, halo and lower alkyl, and X and Y are as above defined.

This invention relates to fungicidal compositions, and methods of making and using the same. More particularly, it relates to compounds and methods for using the same in eliminating certain fungi which are harmful to valuable food crops, but which are substantially nontoxic to the growing crops themselves or to animals or humans.

The compounds of the invention are particularly effective against powdery mildew, tomato late blight and the like. The pathogens giving rise to such conditions constitute pests which have markedly decreased the yield of deciduous fruits such as apples, and of vegetables such as beans, tomatoes and cucumbers.

The fungicidal compositions of the invention can be applied onto the food crop prior to any infection thereof with the pathogen, thus preventing such infection or minimizing its spread. The compounds can also be applied after infection by the fungi has taken place with a marked diminution or elimination of the infection.

The fungicidally active compounds of this invention include 1-substituted anthraquinones and the acyl esters, carbamates and carbonates thereof, wherein the 1-substituted anthraquinones have the formula:

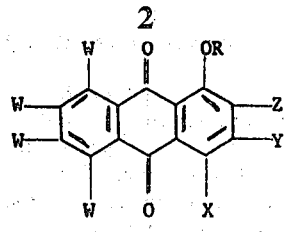

wherein R is hydrogen or acyl, X is halo such as chloro, fluoro or bromo, Z is hydrogen, halo such as chloro, fluoro or bromo, nitro, sulfo or lower alkyl, Y is hydrogen, halo or lower alkyl, and W is hydrogen, hydroxy, halo or lower alkyl.

Certain of the above compounds are novel. The novel compounds are those compounds corresponding to the following formula:

(a) compounds of the formula:

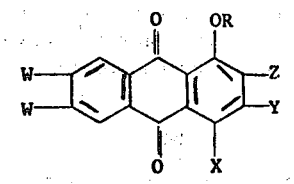

II wherein R is hydrogen or acyl, Y is a member selected from the group consisting of chloro, bromo, fluoro, lower alkyl and hydrogen, Z is a member selected from the group consisting of chloro, bromo, fluoro, nitro, lower alkyl and hydrogen, W is a member selected from the group consisting of chloro and hydrogen with the proviso that when W is chloro, X is a member selected from the group consisting of chloro, bromo and fluoro, and when W is hydrogen, X is fluoro, b. the carbonates, carbamates and metal salts of said group member (a) wherein R is hydrogen, and c. the carbonates and carbamates of the compounds of the formula:

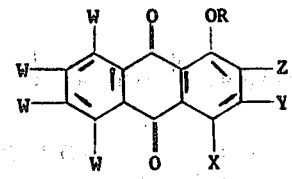

I wherein R is hydrogen, W is a member selected from the group consisting of hydrogen, hydroxy, halo and lower alkyl, and X and Y are as above defined.

Illustrative of the compounds coming within the purview of this invention (Formula I) and having fungicidal activity are the following: 4-chloro-1-hydroxyanthraquinone; 2,4-dichloro-1-hydroxyanthraquinone; 4-bromo-1-hydroxyanthraquinone; 4-chloro-3-methyl-1-hydroxyanthraquinone; 4-chloro-3-methyl-2-bromo-1-hydroxyanthraquinone; 4-chloro-2-bromo-1-hydroxyanthraquinone; 4,5,6,7,8-pentachloro-1-hydroxyanthraquinone; 2,4,5,6,7,8-hexachloro-1-hydroxyanthraquinone; 4,5,6,7,8-pentachloro-3-methyl-1-hydroxyanthraquinone; 4-chloro-3-methyl-2-bromo-1-hydroxyanthraquinone; 4-chloro-3-methyl-2-nitro-1-hydroxyanthraquinone; 4,6-dichloro-1-hydroxyanthraquinone; 4,7-dichloro-3-methyl-1-hydroxyanthraquinone; 2,4,6-trichloro-1-hydroxyanthraquinone; 4,6-dichloro-3-methyl-1-hydroxyanthraquinone; 4-fluoro-1-hydroxyanthraquinone; and the acyl esters, carbamates and carbonates of the above 1-hydroxyanthraquinones.

The invention also encompasses the metal salts of the foregoing compounds and in particular the zinc, calcium, manganese, ferric, copper, sodium and potassium salts. The salts are prepared in the conventional manner, for example in the case of the zinc salt by reaction of diethyl zinc with the corresponding 1-hydroxyanthraquinone. The reaction is conducted under exclusion of oxygen. The diethyl zinc is added to the 1-hydroxyanthraquinone in the form of its partial solution in toluene, benzene or like solvent. The diethyl zinc is added in the stoichiometric quantity in order to produce the desired salt. The salt which then precipitates out is recovered from the reaction mixture in the conventional manner.

The substituted-1-hydroxyanthraquinones of this invention can be prepared by a Friedel-Crafts reaction in the presence of $AlCl_3 \cdot NaCl$ employing as the starting material the appropriate phthalic anhydride and an appropriately substituted phenol, for example as follows:

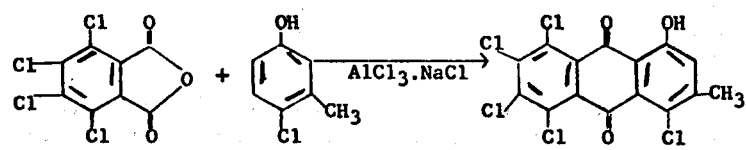

The novel carbamates of the invention can be prepared by reaction of the appropriate carbamyl chloride with the substituted-1-hydroxyanthraquinone in the presence of an acid acceptor such as pyridine, triethylamine and the like. In similar fashion, the carbonate of the invention can be prepared by the reaction of a chloro carbonate with the substituted-1-hydroxyanthraquinone.

Illustrative of the esters, carbamates and carbonates are those wherein R in the above set out formula represents

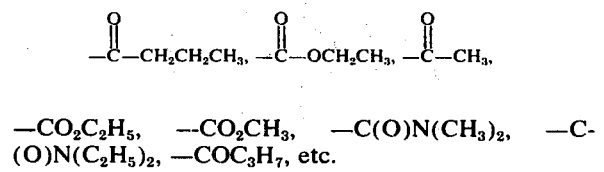

$-CO_2C_2H_5$, $-CO_2CH_3$, $-C(O)N(CH_3)_2$, $-C(O)N(C_2H_5)_2$, $-COC_3H_7$, etc.

The compounds of the invention are applied to the plant to be protected in the form of aqueous dispersions thereof. All of the compounds coming within the above set out formula are water insoluble and must be ground with a suitable surfactant and then spray-dried or similarly treated to obtain wettable powders. The powders can then be extended with the conventional dispersing agents and fillers such as diatomaceous earth, talc, calcium sulfate and the like. At the point of application, the fungicide is rewetted and sprayed onto the foliage using concentrations of 1–125 ppm.

In order to establish the effectiveness of the agents of the invention as mildewcides, screening tests were conducted as follows.

Bean seeds (variety Bountiful) were planted in the conventional manner. Twenty days following planting, the plants were treated in quintuplicate with the test agent using a 150 parts per million in water dispersion with a co-solvent by spraying the first outer trifoliate leaf to the point of run-off. The control plants were sprayed with water.

Thirty days after treatment, the same leaf was inoculated with the bean powdery mildew (Erysiphe polygoni). Eleven days following inoculation, the number of lesions on the leaf were recorded. By comparing the average number of lesions for each agent used to the average obtained for the controls, the percentage of disease reduction was obtained as follows:

$$100 - \left(\frac{100A}{C}\right) = \text{percent disease reduction}$$

where A = number of lesions for agent
C = number of lesions in control

When 1-hydroxy-4-chloroanthraquinone was used as active agent, 11 lesions per leaf were noted, whereas in the controls, 337 lesions per leaf were observed. Thus, 1-hydroxy-4-chloroanthraquinone afforded 97% protection. In the screening, using the test as just described, the following results were obtained:

| Name | Structure | Disease Protection |
|---|---|---|
| 4-chloro-2-methyl-1-hydroxyanthraquinone | 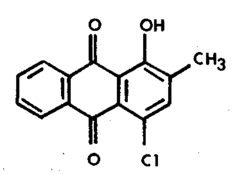 | 93% |
| 2,4,6-trichloro-1-hydroxyanthraquinone | 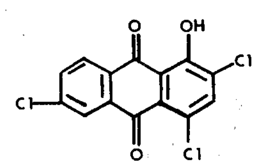 | 99% |

-continued
| Name | Structure | Disease Protection |
|---|---|---|
| 4-chloro-1-hydroxy-anthraquinone | 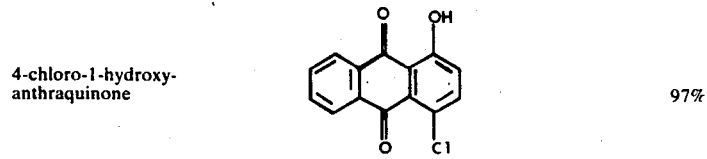 | 97% |
| 4,6-dichloro-1-hydroxy-3-methyl-anthraquinone | 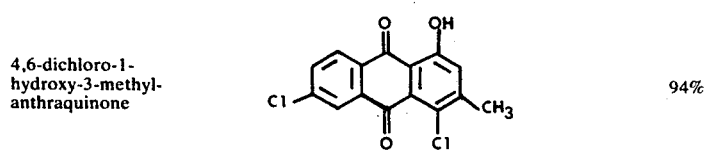 | 94% |
| 3,4-dichloro-1-hydroxyanthra-quinone | 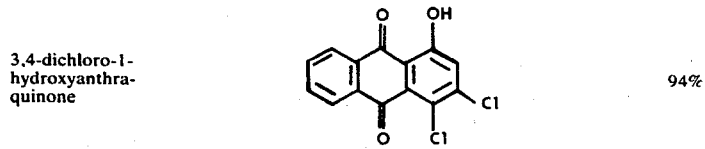 | 94% |
| 4-chloro-3-methyl-1-hydroxyanthra-quinone | 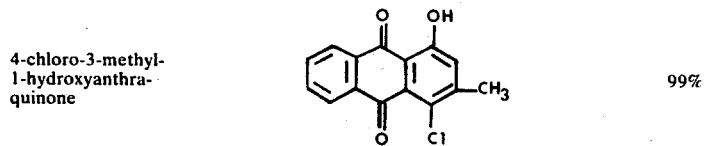 | 99% |
| 4-fluoro-1-hydroxy-anthraquinone | 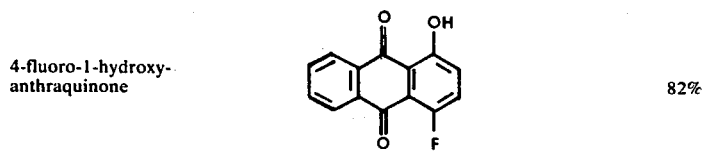 | 82% |
| 4,7-dichloro-1-hydroxyanthra-quinone | 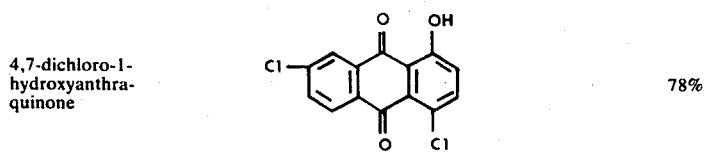 | 78% |
| 1-hydroxyanthra-quinone | 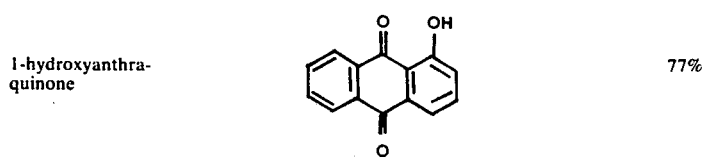 | 77% |
| 2,3,4-dichloro-1-hydroxyanthra-quinone | 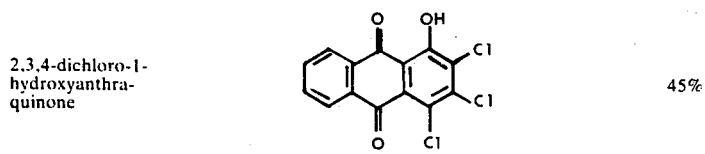 | 45% |

-continued

| Name | Structure | Disease Protection |
|---|---|---|
| 4,5,6,7,8-pentachloro-1-hydroxyanthraquinone | 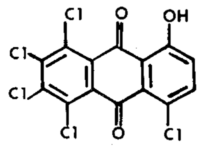 | 46% |
| 4-bromo-1-hydroxyanthraquinone | | 68% |
| 4-bromo-2-sulfo-1-hydroxyanthraquinone sodium salt | 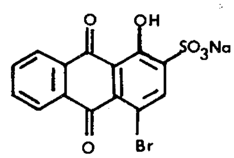 | 70% |
| 3-methyl-4-chloro-1-butyroxy-anthraquinone | 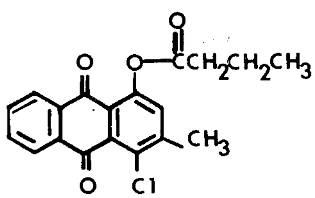 | 43% |
| 2,4-dichloro-1-hydroxyanthraquinone | 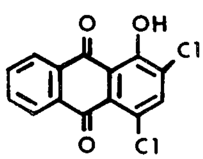 | 26% |
| 2-bromo-4-methyl-1-hydroxyanthraquinone | 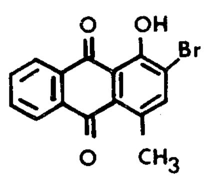 | 55% |
| ethyl, 2,4-dichloro-1-anthraquinonyl carbonate ester | 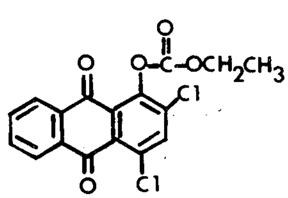 | 34% |
| 2,4-dichloro-1-acetoxy-anthraquinone | 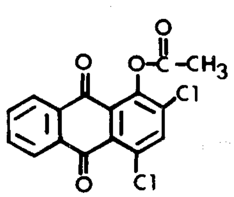 | 32% |

-continued

| Name | Structure | Disease Protection |
|---|---|---|
| 3-methyl-4,5,6,7,8-pentachloro-1-hydroxyanthraquinone | (structure shown) | 20% |

The 1-hydroxy-4-chloro-3-methyl derivative evidenced some systemic effects and, namely, some translocation in the plant with transport of the protective effect. The use of this just mentioned compound as well as of 1-hydroxyanthraquinone resulted in some injury to the plant at the concentration reported. In addition to the protection from infection with fungi as hereinabove set out, the novel compounds of the invention are also able to eradicate the fungi after the same has appeared, i.e., the compounds of the invention have curative powers as well as preventative activity.

The tests carried out in this connection were conducted by planting the same bean seeds as referred to above, thereafter when the same were seven days old, they were inoculated with powdery mildew (Erysiphe polygoni) fungus. After another seven days had elapsed, the bean leaves were treated with the compounds as hereinafter set out, using 150 and 75 parts per million as shown below. The controls were entirely untreated. Toward the end of the fourth week the lesions were counted as above described and the disease reduction similarly calculated. The compounds provided disease reduction as follows:

| Structure | ppm | Disease Reduction, % |
|---|---|---|
| (structure) | 150<br>75 | 100<br>100 |
| (structure) | 150<br>75 | 100<br>100 |
| (structure) | 150<br>75 | 100<br>100 |

In a further series of tests, the following compounds were evaluated for fungicidal activity including foliar, soil and systemic activies:

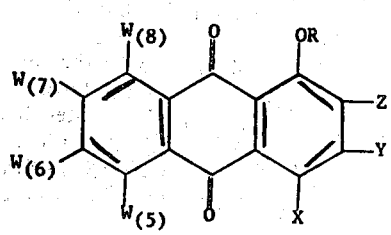

| No. | X | Y | Z | R | W(5) | W(6) | W(7) | W(8) |
|---|---|---|---|---|---|---|---|---|
| 1. | Cl | | | H | OH | | | Cl |
| 2. | Cl | | | H | | | | |
| 3. | Cl | | Cl | CH₂CO₂C₂H₅ | | | | |
| 4. | Br | | SO₃Na | H | | | | |
| 5. | Cl | | NO₂ | H | | | | |
| 6. | Cl | | | H | (zinc salt)* | | | |
| 7. | Cl | | | H | Cl | Cl | Cl | Cl |
| 8. | Cl | CH₃ | | H | | | | |
| 9. | Br | | | H | | | | |
| 10. | Cl | CH₃ | | H | Cl | Cl | Cl | Cl |
| 11. | Cl | Cl | | CH₃COO | Cl | Cl | Cl | Cl |
| 12. | Cl | CH₃ | Cl | CH₃COO | Cl | Cl | Cl | Cl |
| 13. | Cl | | | CO₂C₂H₅ | | | | |
| 14. | Cl | CH₃ | Br | H | | | | |
| 15. | Cl | Cl | Br | H | Cl | Cl | Cl | Cl |
| 16. | Cl | CH₃ | NO₂ | H | | | | |
| 17. | Cl | | Br | H | | | | |
| 18. | Cl | | | CO₂CH₃ | | | | |
| 19. | Cl | CH₃ | | CO₂CH₃ | | | | |
| 20. | Cl | | | C(O)N(CH₃)₂ | | | | |
| 21. | Cl | CH₃ | | C(O)N(CH₃)₂ | | | | |
| 22. | Cl | | Cl | | Cl | Cl | Cl | Cl |

*Compound is in the form of its zinc salt

The compounds displayed varying degrees of activity with compounds Nos. 1, 2, 3, 7, 8, 9, 10, 11, 12, 13, 17, 19 and 21 evidencing particularly favorable activities.

In still another series of experiments, the following compounds were evaluated as foliar protectants against bean and cucumber mildew:

| Compound No. | Rate in ppm | % Disease Control Bean Mildew | % Disease Control Cucumber Mildew |
|---|---|---|---|
| 2 | 300 | 100 | 100 |
| | 75 | 100 | 100 |
| | 19 | 100 | 97 |
| 7 | 300 | 100 | 100 |
| (zinc salt) | 75 | 98 | 100 |
| | 19 | 79 | 97 |
| Untreated | | 100% | Infected |

The following examples are given for further illustrating the invention and are in nowise to be construed as a limitation thereof.

EXAMPLE I

Protection Against Powdery Mildew

Five parts of 1-hydroxy-4-chloroanthraquinone were dissolved in 100 parts of acetone. The resulting solution was poured into 66,000 parts of water under thorough stirring. The suspension thereby obtained was sprayed to incipient run-off on the primary leaves of bean plants. These leaves had previously been infected with the powdery mildew fungus Erysiphe polygoni to the extant that about 20% of the leaf area was covered. The control plants were sprayed with water. In about five days the control plants were 100% infected. The bean plants which has been treated with 1-hydroxy-4-chloroanthraquinone, however, showed only 31% coverage of the leaf area with the pathogen. The bean leaves of the infected plants which had been treated with 1-hydroxy-4-chloroanthraquinone did not possess the white powdery lesions which were easily visible on the untreated control plants. Under the microscope, the infected lesions were observed to have well developed numerous conidia while the treated leaves had very few and then poorly developed conidia.

Conidia which were collected from healthy plants germinated well, while those from the diseased leaves did not germinate.

Control of Erysiphe cichoracearum, i.e., cucumber mildew, using 1-hydroxy-4-chloroanthraquinone was nearly as good as that observed in the case of the bean pathogen.

Powdery mildew on apple leaves was equally well controlled with applications of 75 ppm active ingredient.

Spore germination tests run on both the powdery mildew as mentioned above, established that 4 ppm of 1-hydroxy-4-chloroanthraquinone completely inhibited their germination. At 2 ppm, 1-hydroxy-4-chloroanthraquinone was 90% effective on the bean pathogen but ineffective on the cucumber pathogen.

EXAMPLE 2

The effectiveness of 1-hydroxy-2,4,6-trichloroanthraquinone was tested against wheat rust as an eradicant as follows. Diseased plants were treated at 300 ppm two days after inoculation. After six days the disease reduction was 81%. Similarly the foliage was treated with 150 ppm two days before inoculation with the same wheat rust. After ten days the disease reduction was 94% compared to the controls.

EXAMPLE 3

In the same manner as set out in Example 2, 1-chloro-4-hydroxyanthraquinone was tested for use as a wheat rust eradicant. It provided a 31% disease reduction in each case.

EXAMPLE 4

A mixture of 10.2 g. of 4-chloro-1-hydroxyanthraquinone, 17 g. diethylcarbamyl chloride, and 62 cc. of pyridine were refluxed overnight. The solution which was obtained was cooled and added to 400 cc. of water containing 50 cc. concentrated HCl. Following filtration, the tan filter cake was washed with water and dried. A new compound, 4-chloro-1-anthraquinonyl diethylcarbamate having a melting point of 148°–150°C was recovered.

| Analysis | Calc'd | Found |
|---|---|---|
| C | 65.7 | 64.64 |
| H | 4.68 | 4.48 |
| N | 4.11 | 5.0 |
| Cl | 10.42 | 9.86 |

EXAMPLE 5

Employing the same procedure set out in Example 2, 4-chloro-3-methyl-1-anthraquinonyl diethylcarbamate was prepared by the reaction of diethylcarbamyl chloride with 4-chloro-3-methyl-1-hydroxyanthraquinone. The melting point of the novel 2,4-chloro-3-methyl-1-anthraquinonyl-diethylcarbamate thereby obtained was 165°–168°C.

| Analysis | Calc'd | Found |
| --- | --- | --- |
| C | 64.5 | 64.05 |
| N | 3.78 | 3.84 |
| Cl | 9.45 | 9.42 |
| H | 4.35 | 4.93 |

EXAMPLE 6

The same procedure as set out in Example 2 was followed and 4-chloro-1-anthraquinonyl dimethylcarbamate having a melting point of 182°–184°C was obtained by reacting dimethylcarbamyl chloride with 4-chloro-hydroxyanthraquinone.

EXAMPLE 7

Analogously to Example 2, 4-chloro-3-methyl-1anthraquinonyl carbamate having a melting point of 192°–198°C was prepared by reacting dimethylcarbamyl chloride with 4-chloro-3-methyl-1-hydroxyanthraquinone.

EXAMPLE 8

Using the procedure of Example 2, 2,4-dichloro-1-anthraquinonyl dimethylcarbamate having a melting point of 225°–230°C was prepared by reaction of dimethylcarbamyl chloride with 2,4-dichloro-1-hydroxyanthraquinone.

EXAMPLE 9

The process of Example 2 was followed but reacting in this instance piperidinyl carbamyl chloride and 4-chloro-1-hydroxyanthraquinone to produce 4-chloro-1-anthraquinonyl piperdinyl carbamate having a melting point of 195°–199°C.

EXAMPLE 10

A mixture of 13 g. 4-chloro-1-hydroxyanthraquinone, 225 cc. acetone, 10 g. triethylamine and 11 g. of ethyl chloro carbonate were refluxed. The resultant solution was filtered to remove the triethylamine hydrochloride and starting anthraquinone present, the filtrate evaporated to dryness and slurried with a water and acetone mixture. The resultant slurry was filtered, the solid material washed with water and dried. The yield of 4-chloro-1-anthraquinonyl ethyl carbonate having a melting point of 112°–115°C amounted to 9g.

| Analysis | Calc'd | Found |
| --- | --- | --- |
| C | 61.8 | 61.64 |
| H | 3.3 | 3.76 |
| Cl | 10.6 | 10.05 |

EXAMPLES 11–15

Employing the same procedure as discussed in Example 9, the following carbonates were prepared:

4-chloro-3-methyl-1-anthraquinonyl ethyl carbonate having a melting point of 150°–154°C was prepared by the reaction of ethyl chlorocarbonate with 4-chloro-3-methyl-1-hydroxyanthraquinone.

4-chloro-1-anthraquinonyl methyl carbonate having a melting point of 230°–235°C was prepared by reaction of methyl chlorocarbonate with 4-chloro-1-hydroxyanthraquinone.

4-chloro-3-methyl-anthraquinonyl methyl carbonate having a melting point of 152°–155°C was prepared by reaction of ethyl chlorocarbonate with 4-chloro-3-methyl-1-hydroxyanthraquinone.

2,4-dichloro-1-anthraquinonyl ethyl carbonate having a melting point of 132°–142°C was prepared by reaction of ethyl chlorocarbonate with 2,4-dichloro-1-hydroxyanthraquinone.

2,4-dichloro-1-anthraquinonyl n-butyl carbonate having a melting point of 90°–97°C was prepared by reaction of n-butyl chlorocarbonate with 2,4-dichloro-1-hydroxyanthraquinone.

What is claimed is:

1. A fungicidal composition comprising a fungicidal amount of a compound selected from the group consisting of
   a. a compound of the formula:

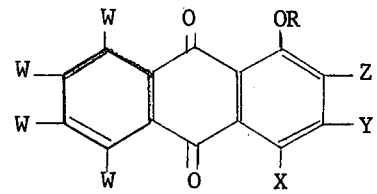

wherein R is a member selected from the group consisting of hydrogen and acyl having 2 to 4 carbon atoms; X is a member selected from the group consisting of chloro, fluoro and bromo; Z is a member selected from the group consisting of hydrogen, chloro, fluoro, bromo, nitro, sodium sulfo and lower alkyl; Y is a member selected from the group consisting of hydrogen, halo and lower alkyl; and W is a member selected from the group consisting of hydrogen, hydroxy, halo and lower alkyl; and
   b. a metal salt thereof selected from the group consisting of zinc, calcium, ferric, manganese, sodium, potassium and copper in admixture with a suitable carrier therefor.

2. The composition according to claim 1 wherein said compound is 2,4,6-trichloro-1-hydroxyanthraquinone.

3. The composition according to claim 1 wherein said compound is 4,6-dichloro-3-methyl-1-hydroxyanthraquinone.

4. The composition according to claim 1 wherein said compound is 4-chloro-3-methyl-1-hydroxyanthraquinone.

5. The composition according to claim 1 wherein said compound is 4-fluoro-1-hydroxyanthraquinone.

6. The composition according to claim 1 when said compound is 4,7-dichloro-1-hydroxyanthraquinone.

7. A method of combating fungus infections which comprises applying to plants having such infection a fungicidally effective amount of a composition according to claim 1.

* * * * *